(12) United States Patent
Gratz et al.

(10) Patent No.: US 11,622,546 B2
(45) Date of Patent: Apr. 11, 2023

(54) HUMANIZED MOUSE MODEL

(71) Applicant: DEBRA Austria, Hilfe bei Epidermolysis bullosa, Vienna (AT)

(72) Inventors: Iris Gratz, Salzburg (AT); Maria Klicznik, Salzburg (AT); Eva Murauer, Carnon (FR)

(73) Assignee: DEBRA AUSTRIA, HILFE BEI EPIDERMOLYSIS BULLOSA, Vienna (AT)

( * ) Notice: Subject to any disclaimer, the term of this patent is extended or adjusted under 35 U.S.C. 154(b) by 456 days.

(21) Appl. No.: 16/389,821

(22) Filed: Apr. 19, 2019

(65) Prior Publication Data
US 2019/0320629 A1 Oct. 24, 2019

(30) Foreign Application Priority Data

Apr. 19, 2018 (EP) .................................... 18168258

(51) Int. Cl.
| | | |
|---|---|---|
| A01K 67/027 | (2006.01) |
| C12N 15/85 | (2006.01) |
| A01N 1/02 | (2006.01) |
| C12N 5/071 | (2010.01) |
| C12N 5/0781 | (2010.01) |
| C12N 5/0783 | (2010.01) |
| C12N 5/0784 | (2010.01) |
| C12N 5/0786 | (2010.01) |
| C12N 5/077 | (2010.01) |
| G01N 33/50 | (2006.01) |

(52) U.S. Cl.
CPC ........ *A01K 67/0275* (2013.01); *A01N 1/0221* (2013.01); *C12N 5/0629* (2013.01); *C12N 5/0635* (2013.01); *C12N 5/0636* (2013.01); *C12N 5/0639* (2013.01); *C12N 5/0645* (2013.01); *C12N 5/0646* (2013.01); *C12N 5/0656* (2013.01); *G01N 33/5008* (2013.01); *A01K 2227/105* (2013.01); *A01K 2267/03* (2013.01)

(58) Field of Classification Search
None
See application file for complete search history.

(56) References Cited

U.S. PATENT DOCUMENTS 5,602,305 A 2/1997 Pober et al.
2011/0113496 A1 5/2011 Shultz et al.

OTHER PUBLICATIONS

Mammal—Wikipedia p. 1 of 27 downloaded Sep. 7, 2021.*
NSG mouse—Wikipedia p. 1 of 5; downloaded Sep. 7, 2021.*
Severe combined immunodeficient mice—Wikipedia p. 1 of 4; downloaded Sep. 7, 2021.*
Wang et al., Spontaneous Cell Sorting of Fibroblasts and Keratinocytes Creates an Organotypic Human Skin Equivalent Journal of Investigative Dermatology vol. 114, Issue 4, Apr. 2000, pp. 674-680.*
Acosta-Rodriguez et al, "Surface phenotype and antigenic specificity of human interleukin 17-producing T helper memory cells", 2007, Nat. Immunol., vol. 8, No. 6, pp. 639-646.
Carretero et al, "Differential Features between Chronic Skin Inflammatory Diseases Revealed in Skin-Humanized Psoriasis and Atopic Dermatitis Mouse Models", 2016, J. Invest. Dermatol., vol. 136, No. 1, pp. 136-145.
Centlivre et al, "Analysis of the skin of mice humanized for the immunie system", 2017, Experimental Dermatology, vol. 26, No. 10, pp. 963-966.
Daley et al, "Use of Ly6G-specific monoclonal antibody to deplete neutrophils in mice", 2008, J. Leukoc. Biol., vol. 83, No. 1, pp. 64-70.
Fahy et al, "Chemokine-Induced Cutaneous Inflammatory Cell Infiltration in a Model of Hu-PBMC-SCID Mice Grafted with Human Skin", 2001, American J. of Pathol., vol. 158, No. 3, pp. 1053-1063.
Garcia et al, "Humanized mice: Current states and perspectives", 2012, Immunol. Lett., vol. 146, No. 1-2, pp. 1-7.
Hammad et al, "Human Dendritic Cells in the Severe Combined Immunodeficiency Mouse Model: Their Potentiating Role in the Allergic Reaction", 2000, Laboratory Investigation, vol. 80, No. 4, pp. 605-614.
Harui et al, "Reconstitution of huPBL-NSG Mice with Donor-Matched Dendritic Cells Enables Antigen-Specific T-cell Activation", 2011, J. Neuroimmune Pharmacol., vol. 6, pp. 148-157.
Kenney et al, "Humanized Mouse Models for Transplant Immunology", 2015, American J of Transplantation, vol. 16, No. 2, pp. 389-397.
King et al, A new Hu-PBL model for the study of human islet alloreactivity based onNOD-scid mice bearing a targeted mutation in the IL-2 receptor gamma chain gene, 2008, Clinical Immunology, vol. 126, pp. 303-314.
Lee et al, "Engrafted human cells generate adaptive immune responses to *Mycobacterium bovis* BCG infection in humanized mice", 2013, BMC Immunol., vol. 14, p. 53.
Merkley et al, "Large-scale analysis of protein expression changes in human keratinocytes immortalized by human papilloma virus type 16 E6 and E7 oncogenes", 2009, Proteome Sci, vol. 7, p. 29.
Pearson et al, "Creation of "Humanized" Mice to Study Human Immunity", 2008, Curr Protoc Immunol., Chapter 15: Unit 15.21 (doi:10.1002/0471142735.im1521s81).
Pino et al, "Development of Novel Major Histocompatibility Complex Class I and Class II-Deficient NOD-SCID IL2R Gamma Chain Knockout Mice for Modeling Human Xenogeneic Graft-Versus-Host Disease", 2010, Methods Mol. Biol., vol. 602, pp. 105-117.
Sanchez Rodriguez et al, "Memory regulatory T cells reside in human skin", 2014, The J. of Clin. Invest., vol. 124, No. 3, pp. 1027-1036.
Shultz et al, "Human Lymphoid and Myeloid Cell Development in NOD/LtSz-scid IL2Rγnull Mice Engrafted with Mobilized Human Hemopoietic Stem Cells1,2", 2005, The J. of Immunol., vol. 174, No. 10, pp. 6477-6489.

(Continued)

*Primary Examiner* — Maria G Leavitt
(74) *Attorney, Agent, or Firm* — Loza & Loza, LLP; Michael F. Fedrick

(57) ABSTRACT

A non-human mammalian model for human diseases or disorders comprising a non-human neutrophil depleted mammalian host engrafted with a human skin equivalent (huSE) and human immune cells.

10 Claims, 7 Drawing Sheets

(56) References Cited

OTHER PUBLICATIONS

Shultz et al, "Humanized mice in translational biomedical research", 2007, Nat. Rev. Immunol., vol. 7, No. 2, pp. 118-130.

Shutlz et al, "Humanized mice for immune system investigation: progress, promise and challenges", 2012, Rev. Immunol., vol. 12, No. 11, pp. 786-798.

Smithson et al, "Molecular analysis of the heavy chain of antibodies that recognize the capsular polysaccharide of Neisseria meningitidis in hu-PBMC reconstituted SCID mice and in the immunized human donor", 1999, Mol. Immunol., vol. 36, No. 2, pp. 113-124.

Sunaga et al, "Reconstitution of Human Keloids in Mouse Skin", 2017, PRS Global Open, vol. 5, No. 4, pp. e1304.

Racki et al, NOD-scid IL2rynull (NSG) Mouse Model of Human Skin Transplantation and Allograft Rejection:, 2010, Transplantation, vol. 89, No. 5, pp. 527-536.

Wang et al, "Spontaneous Cell Sorting of Fibroblasts and Keratinocytes Creates an Organotypic Human Skin Equivalent", 2000, Journal of Investigative Dermatology, vol. 114, No. 4, pp. 674-680.

Watanabe et al, "Human skin is protected by four functionally and phenotypically discrete populations of resident and recirculating memory T cells", 2015, Sci. Transl. Med , vol. 7, No. 279: 279ra39 (doi:10.1126/scitranslmed.3010302).

Zhang et al, "Tissue Engineered Human Skin Equivalents", 2012, Pharmaceutics, vol. 4, No. 1, pp. 26-41 (doi:10.3390/pharmaceutics4010026).

Extended European Search Report for related Patent Application No. 18168258.4 dated Jul. 6, 2018; 8 pages.

Klicznik et al., Sci Rep., 2020, 10:111164.

\* cited by examiner

HUMANIZED MOUSE MODEL

CROSS-REFERENCE TO RELATED APPLICATIONS

This application claims the benefit of priority under 35 U.S.C. § 119 from European Patent Application No. 18168258.4, filed Apr. 19, 2018. The disclosure of the foregoing application is incorporated herein by reference in its entirety.

FIELD OF THE INVENTION

The present invention relates to a non-human mammalian model for human diseases or disorders comprising a non-human neutrophil depleted mammalian host engrafted with a human skin equivalent (huSE) and human immune cells, its method of production, and uses of the model.

BACKGROUND ART

The skin functions as the primary barrier between an organism and the outside world. Although it is home to a robust and diverse community of commensal microorganisms, it must also prevent entry of environmental toxins, irritants, and numerous viral, bacterial and parasitic pathogens. To effectively maintain its barrier function, the skin must undergo rapid and highly efficient tissue repair when damaged or compromised. This is associated with local antimicrobial and inflammatory responses that help prevent or combat concurrent infection.

Consistent with its functions in maintaining barrier integrity and preventing infection, the skin is home to a number of specialized T cell populations, including conventional CD4+ and CD8+ memory T cells (both recirculating and tissue-resident memory (TRM) populations), Foxp3+ regulatory T cells, and several populations of skin T cells. In healthy individuals these cells do not only combat infection and help to eliminate tumor cells but also work in concert to help maintain normal tissue homeostasis and promote wound repair. However, despite significant advances in understanding cutaneous immunity, the specific functions of different populations of cutaneous T cells, their roles in maintaining normal skin homeostasis, and contributions to inflammatory diseases of the skin remain poorly understood.

Wang et al. created a method to generate an organotypic human skin equivalent, wherein a cell slurry containing human keratinocytes and human fibroblasts is added to silicone chambers implanted on the back of immunodeficient mice (Wang et al., Journal of Investigative Dermatology (2000) Vol. 114, 4:674-680).

King et al. engrafted immunodeficient NOD/SCID/IL2r-$\gamma^{null}$ (NSG) mice with human peripheral blood lymphocytes and showed that the engrafted human lymphocytes retained function because the humanized mice were able to reject human islet allografts (King et al. Clinical Immunology (2008) 126, 303-314).

Harui et al. engrafted immunodeficient NOD/SCID/IL2r-$\gamma^{null}$ (NSG) mice with human peripheral blood lymphocytes in combination with donor-matched monocyte derived dendritic cells to reconstitute antigen responsiveness and to allow in vivo assessment of human immune response to viruses, vaccines, and other immune challenges (Harui et al., J Neuroimmune Pharmacol (2011) 6:148-157).

Reliance on conventional animal models for skin research can be problematic due to fundamental structural differences in the skin in humans vs. mice, and a lack of direct correspondence between cutaneous T cell populations in these species. Obvious ethical considerations constrain direct analysis and manipulation of immune responses in humans.

More and more groups are studying the skin based on its obvious clinical relevance as a barrier organ, a target-organ of autoimmunity and because of the high incidence of skin cancer. However, currently published humanized mouse models suffer from various limitations and no available model allows researchers to study the role of individual, specific immune cell types within the tissue or also the interaction of select immune cells within the tissue.

Thus there is a clear need of a humanized animal model, which allows the study of the function of human skin homing and human skin resident immune cells.

SUMMARY OF INVENTION

It is an objective of the present invention to provide a non-human mammalian model to study and manipulate immune responses in engineered human skin.

The objective is solved by the subject matter of the present invention.

According to the invention there is provided a non-human mammalian model for human diseases or disorders comprising a non-human neutrophil depleted mammalian host engrafted with a human skin equivalent (huSE) and human immune cells.

According to a further embodiment of the invention as described herein, the human immune cells are selected from the group consisting of T cells, B cells, natural killer cells, monocytes, monocyte derived dendritic cells, dendritic cells and their subtypes, tissue-derived dendritic cells, Langerhans cells, γδ-T cells, mast cells, innate lymphoid cells (ILC), and human peripheral blood mononuclear cells (huPBMC).

According to a further embodiment of the invention as described herein, the mammalian host is a rodent, preferably a mouse, preferably an immunodeficient mouse, preferably selected from the group consisting of NOD Scid common-γ chain-/- (NSG) mouse, NOD Shi-scid common-γ chain-/- (NOG) mouse, and BALB/cA-Rag2-/- IL2rgamma-/- (BRG) mouse.

According to a further embodiment of the invention as described herein, the human skin equivalent (huSE) comprises human keratinocytes and human fibroblasts. Specifically, said huSE comprises human primary or immortalized keratinocytes and human primary or immortalized fibroblasts. Specifically, said huSE comprises primary keratinocytes and primary fibroblasts or immortalized keratinocytes and immortalized fibroblasts. Specifically, said huSE can comprise a mix of primary keratinocytes and immortalized fibroblasts or immortalized keratinocytes and primary fibroblasts.

Specifically, further cell types can be added to the cell slurry forming the huSE. Preferably, further skin cell types are added to the huSE. Skin cells added to the huSE are healthy, malignant or comprise a genetic modification. Specifically, such further cell types can be skin cells such as keratinocyte stem cells, melanocytes, pericytes, blood-vessel stem cells, mesenchymal stem cells (MCS or MSPC) and/or malignant skin cells such as primary squamous cell cancer (SCC), basal cell cancer (BCC) or melanoma cells or SCC, BCC or melanoma cell lines and/or immune cells such as T cells, B cells, natural killer cells, monocytes, monocyte derived dendritic cells, dendritic cells and their subtypes, tissue-derived dendritic cells, Langerhans cells, γδ-T cells, mast cells, innate lymphoid cells (ILC), and human peripheral blood mononuclear cells (huPBMC) and/or other human cell types.

Specifically, the genetic modification of skin cells comprised in the huSE can be a genetic modification arising naturally in disease, or the genetic modification can be introduced artificially. Preferably, the genetic modification is introduced using methyltransferases, kinases, CRISPR/Cas9, multiplex automated genome engineering (MAGE), conjugative assembly genome engineering (CAGE), the Argonaute protein (Ago) or a derivative thereof, zinc-finger nucleases (ZFNs) or transcription activator-like effector nucleases (TALENs).

Specifically, said human skin equivalent is an organotypic human skin equivalent.

According to a further embodiment of the invention as described herein, said huSE and said immune cells are derived from the same donor (autologous) or from different donors (allogeneic).

According to a further embodiment, further cell types added to the cell slurry forming the huSE can be derived from the same donor (autologous) as the donor of the keratinocytes, fibroblasts and/or immune cells or from a different donor (allogeneic). Specifically, each cell type added to the cell slurry forming the huSE can be derived from a different donor.

Further provided herein is a method of generating a non-human mammalian model, comprising the steps of
  a. in vitro expanding keratinocytes and fibroblasts which have been provided from a human donor,
  b. engrafting a non-human mammalian host with the in vitro expanded keratinocytes and fibroblasts derived in step a, thereby generating a human skin equivalent (huSE),
  c. engrafting the non-human mammalian host of step b with human immune cells, and
  d. depleting host neutrophils.

According to a further embodiment of the invention as described herein, the non-human mammalian host is engrafted with organotypic human skin equivalent using grafting chambers loaded with a cell slurry comprising human keratinocytes and human fibroblasts. Specifically, the non-human mammalian host is engrafted with human skin equivalent using grafting chambers loaded with a cell slurry comprising at least $1\times10^6$ primary or immortalized human keratinocytes and at least $1\times10^6$ primary or immortalized human fibroblasts. Specifically, said cell slurry comprises at least $1\times10^5$, $5\times10^5$, $1\times10^6$, $5\times10^6$ or $1\times10^7$ primary or immortalized human keratinocytes. Specifically, said cell slurry comprises at least $1\times10^5$, $5\times10^5$, $1\times10^6$, $5\times10^6$ or $1\times10^7$ primary or immortalized human fibroblasts.

According to a specific embodiment the non-human mammalian host is engrafted with human skin equivalent using grafting chambers loaded with a cell slurry comprising not more than $5\times10^6$ fibroblasts and $5\times10^6$ keratinocytes, preferably not more than $3\times10^6$ fibroblasts and $3\times10^6$ keratinocytes and even more preferably not more than $1\times10^6$ fibroblasts and $1\times10^6$ keratinocytes.

According to a further embodiment of the invention as described herein, the non-human mammalian host is engrafted with at least $1\times10^6$ human immune cells, selected from the group consisting of T cells, B cells, natural killer cells, monocytes, monocyte derived dendritic cells, dendritic cells and their subtypes, tissue-derived dendritic cells, Langerhans cells, γδ-T cells, mast cells, innate lymphoid cells (ILC), and human peripheral blood mononuclear cells (huPBMC). Specifically, the non-human mammalian host is engrafted with only one type of human immune cells or with multiple types of human immune cells. Specifically, at least $1\times10^5$, $0.5\times10^6$, $1\times10^6$, $5\times10^6$ or $1\times10^7$ human immune cells are engrafted.

According to a further embodiment of the invention as described herein, said human immune cells are frozen in an aqueous solution after isolation and thawed in resting media before engrafting the human immune cells into the non-human mammalian host.

According to a further embodiment of the invention as described herein, the host neutrophils are depleted by administration of an antibody, preferably an anti-granulocyte receptor-1 (Gr-1) antibody.

According to a further embodiment of the invention as described herein, the non-human mammalian host is an immunodeficient mouse, preferably selected from the group consisting of NOD Scid common-γ chain$^{-/-}$ (NSG) mouse, NOD Shi-scid common-γ chain$^{-/-}$ (NOG) mouse, and BALB/cA-Rag2$^{-/-}$ IL2rgamma$^{-/-}$ (BRG) mouse.

According to a further embodiment of the invention the non-human mammalian model provided herein is used as an animal model for skin related diseases or disorders.

Specifically, the non-human mammalian model provided herein is used for the study of immune-mediated skin diseases, including skin related autoimmune diseases and allograft rejection, genodermatoses or malignant skin diseases.

Specifically, the immune-mediated skin disease can be psoriasis, vitiligo or lupus.

Specifically, the genodermatosis can be epidermolysis bullosa, ichthyosis, palmoplantar keratoderma, neurofibromatosis, xeroderma pigmentosum, incontinentia pigmenti, restricitive dermopathy or pachyonychia congenital.

Specifically, the malignant skin disease can be basal cell carcinoma, squamous cell carcinoma, melanoma, Merkel cell carcinoma, sarcoma, cutaneous skin lymphoma or skin adnexal tumors.

According to a further embodiment of the invention the non-human mammalian model provided herein is used for the study of the function of human skin homing and skin resident immune cells, the reaction of skin resident immune cells in response to allergens, the function of skin resident immune cells in wound repair, hair follicle development, infection or cancer development.

According to a further embodiment of the invention the non-human mammalian model provided herein is used for studying pharmaceuticals, cell products, biologics or small molecules (organic compounds having a low molecular weight, generally <900 daltons) targeting skin cells, or delivery systems such as nanoparticles, microbubbles, microneedles or gene guns.

DETAILED DESCRIPTION

Figure 1:
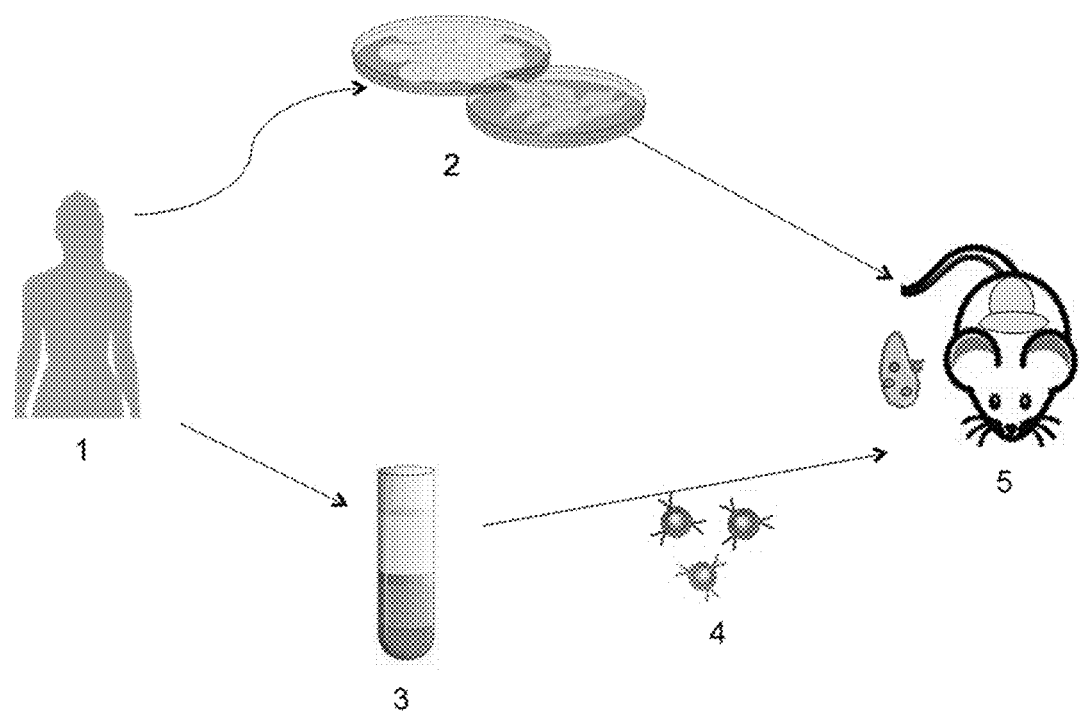
FIG. 1 depicts the humanized mouse model. Fibroblasts and keratinocytes are isolated from the human skin of donors and expanded in vitro (either unaltered or after immortalization). Keratinocytes and fibroblasts are then grafted onto the backs of immuno-deficient NSG (NOD Scid common γ chain knockout) mice using a grafting chamber to form a skin equivalent (SE) (see FIG. 2). Additionally, immune cells are isolated from the peripheral blood of the same donor (autologous) and adoptively transferred into the same immuno-deficient NSG mice. We can then follow the transferred cells in the graft and lymphoid organ (i.e. the spleen) of the mice.

To overcome the shortcomings of currently available mouse models, a humanized animal model, which allows study of the function of human skin homing and skin resident immune cells, was developed. In this humanized animal model engineered human skin equivalents are engrafted onto NSG non-human mammals to probe the response of adoptively transferred human immune cells in the skin tissue. This allows mechanistic studies of skin related human immune responses in vivo. Particularly, the model is designed to follow antigen-specific immune responses in human skin as well as the trafficking behavior of skin-tropic cells (such as CLA+ cells) and their function during cutaneous tissue-repair responses.

Thus, in a preferred embodiment, the model is designed to provide important new insights into how cutaneous immune cells such as T cells modulate the host-protective and tissue-repair responses in response to insults such as wounding, infection or cancer development. In this preferred embodiment, the model helps to identify new cellular and molecular targets to therapeutically stimulate skin-immunity to support wound-healing or cancer responses and also optimize the development and function of engineered skin tissue grafts.

The non-human mammalian model of the invention overcomes the inherent limitations that result from fundamental structural differences in the skin of humans vs. for example mice, and a lack of direct correspondence between cutaneous T cell populations in these species.

Obvious ethical and legal aspects constrain direct analysis and manipulation of immune responses in humans. Therefore, the host of the model of the invention is not human, but it is a humanized host.

In a specific embodiment of the invention the host of the non-human mammalian model is a rodent. The rodent host can be selected from the group consisting of mice, rats, squirrels, porcupines, beavers, guinea pigs and hamsters. Preferably, the host is a mouse or rat.

In one embodiment, the host of the non-human mammalian model is a mouse. Specifically, the host is an immunodeficient mouse. In order to achieve humanized mouse models researchers have developed immunodeficient recipient strain such as the NOD Scid common-γ chain$^{-/-}$ (NSG) mouse, NOD Shi-scid common-γ chain$^{-/-}$ (NOG) mouse, and BALB/cA-Rag2$^{-/-}$ IL2rgamma$^{-/-}$ (BRG) mouse. The derivation and unique characteristics of the immunodeficient mouse models derived from immunodeficient Il2rg$^{null}$ mice have been reviewed in detail (1). Il2rg$^{null}$ mice lack mature T cells, B cells and natural killer (NK) cells and, in addition, they have many defects in innate immunity.

For example, strains of NSG and BRG mice are available from The Jackson Laboratory (http://www.jax.org) and NOG mice are available from Taconic (http://www.taconic.com).

In a further embodiment the host of the non-human mammalian model can be an immunodeficient rabbit, hare, monkey or other mammal which is not a human.

Specifically, said non-human mammalian host is neutrophil depleted. Despite the fact that immunodeficient Il2rg$^{null}$ mice are highly immunodeficient, they still produce a viable granulocyte/neutrophil population that can mediate some degree of host-versus-graft-disease leading to the rejection and poor engraftment of human immune cells. In order to minimize this response, neutrophils are depleted in the non-human mammalian host. Depletion of neutrophils can be achieved with different methods, employing agents that specifically bind to neutrophils. Such depletion is preferably achieved using antibodies. Preferably, neutrophils are depleted using an anti-granulocyte receptor-1 (Gr-1) monoclonal antibody or an anti-Ly6G monoclonal antibody.

The host of the non-human mammalian model is engrafted with a human skin equivalent (huSE). A human skin equivalent comprises a plurality of keratinocytes joined by cell-cell adhesions, preferably together with fibroblasts and other cells, which are obtained from a human or which are the progeny of cells obtained from a human (either normal or malignant, and either with or without artificially induced genetic modifications). Engraftment as referred to herein means the placement or production of an huSE on a host animal, preferably on, over, or in place of the epidermis and/or dermis of the host. At the time of engraftment, the human skin equivalent of the present invention is free of skin resident immune cells.

Such a "blank slate" tissue, i.e. tissue without any resident immune cells, has the advantage that only the immune cells co-engrafted into the non-human mammalian host inhabit the skin tissue. Surprisingly, host immune cells do not infiltrate the human skin tissue; only engrafted human immune cells migrate to the human skin tissue. Surprisingly, engrafted human immune cells only infiltrate the human skin equivalent, and not non-human host tissue. Therefore, this model can be used to study specific skin related human immune responses, without the interference of host immune cells.

Specifically, the human skin equivalent can be generated using 3D skin-cultures devoid of immune cells grown in vitro or using grafting chambers.

Preferably grafting chambers are used. Specifically, the huSE is generated by loading a cell slurry containing both, human keratinocytes and human fibroblasts, into grafting chambers, which have been implanted on the back of the immunodeficient host. Within 4 weeks this cell slurry sorts out to reconstitute a clearly defined dermis and stratified epidermis. Preferably, the grafting chamber is removed after 7 days. Approximately 25 to 35 days after engraftment the human skin is fully developed and has fully healed in. Specifically, this method generates a cell-sorted organotypic human skin equivalent. The two cell types sort into two clearly defined layers of dermis and epidermis. The morphology of the organotypic human skin equivalent parallels normal human full-thickness skin.

Rather than grafting 3D-skin cultures as reported previously (9), the use of grafting chambers is an easier approach to provide comparable skin generation. Herein the use of grafting chambers is established to create human skin equivalents on NSG mice. Specifically, skin cells, preferably either primary or immortalized keratinocytes and fibroblasts, are expanded in vitro. A 1:1-mix of both cell types is then placed in silicone chambers on the back of recipient mice. These cells then sort spontaneously and differentiate into skin tissue.

In addition to using primary cells from healthy donors also immortalized primary keratinocytes or immortalized primary fibroblasts derived from either patients or healthy donors can be used to produce such human skin equivalent. Specifically, human keratinocytes and fibroblasts can be immortalized through the introduction of viral genes deregulating the cell cycle or expression of key proteins required for immortality, such as telomerase. Immortalization can further be achieved through a variety of cellular events including telomere length stabilization, epigenetic gene silencing by selective promoter methylation, oxidative DNA damage, and inactivation of cell cycle regulatory genes or overexpression of cellular or viral oncogenes. T antigen from simian virus 40 (SV40), E6 and E7 from human papillomavirus (HPV), and E1A and E1B from adenovirus are well-characterized viral oncogenes which induce immortalization of host cells.

In a preferred embodiment, human primary keratinocytes are immortalized using human papilloma virus type 16 E6 and E7 oncogenes. In a further preferred embodiment, human primary fibroblasts are immortalized through introduction of the viral oncoprotein simian virus 40 (SV40) large T-antigen. In a further preferred embodiment, primary cells, such as keratinocytes or fibroblasts, are immortalized through heterologous expression of human telomerase transcriptase (huTERT).

Use of immortalized cells provides the clear advantage that disease models can be studied without having to use rare and limited patient material. Specifically, the behavior (e.g. maintenance, activations status, migration) of autologous skin resident T cells in human skin that exhibits the features of a particular disease can be studied.

Such human skin equivalent can be modified for the study of various skin-related diseases or disorders. For example, additional cell types can be added to the cell slurry. Specifically, such cell types can be healthy or malignant skin cells or immune cells. Accurate modeling of genetic skin diseases can be achieved by mixing normal cells with the patient cell type expressing a mutant gene. Specifically, cells used in the model can be genetically modified. Specifically, immortalized keratinocytes or fibroblasts can be genetically modified.

Specifically, such genetic modification can be achieved using methyltransferases, kinases, CRISPR/Cas9, multiplex automated genome engineering (MAGE), conjugative assembly genome engineering (CAGE), the Argonaute protein (Ago) or a derivative thereof, zinc-finger nucleases (ZFNs) or transcription activator-like effector nucleases (TALENs). Preferably, CRISPR/Cas9 is used to introduce specific mutations into cells of the human skin equivalent. CRISPR/Cas9 refers to a gene editing method well known to those skilled in the art, as well as modifications thereof. Such modifications include, but are not limited to, fusion of a nuclease-dead Cas9 (dCas9) to cytidine deaminase, enabling site-specific conversion of cytidine to uracil and mutations to the Cas9 protein, which generate versions of the Cas9 protein that only create single-strand DNA cuts (nicks).

Surprisingly, the use of immortalized keratinocyte and fibroblast cells instead of primary cells has no apparent impact on tissue generation or the phenotype of skin-resident immune cells. Use of immortalized cells allows the researcher to create tissues that are deficient in any desired gene by employing gene editing methods such as CRISPR/Cas9. Using this approach, a system to study the behavior (e.g. maintenance, activation status, migration) of autologous skin resident T cells in human skin that exhibits the features of a particular disease without the limitations of having to use rare and limited patient material.

The non-human mammalian model further comprises human immune cells. Specifically, human immune cells used in the model of the invention can be human T cells, B cells, natural killer cells, monocytes, monocyte derived dendritic cells, dendritic cells and their subtypes, tissue-derived dendritic cells, Langerhans cells, γδ-T cells mast cells, innate lymphoid cells (ILC), and human peripheral blood mononuclear cells (huPBMC).

In a preferred embodiment, huPBMC are used. Specifically, peripheral blood mononuclear cell (PBMC) is any peripheral blood cell having a round nucleus. These cells consist of lymphocytes (T cells, B cells, NK cells) and monocytes, whereas erythrocytes and platelets have no nuclei, and granulocytes (neutrophils, basophils, and eosinophils) have multi-lobed nuclei. In humans, lymphocytes make up the majority of the PBMC population, followed by monocytes, and only a small percentage of dendritic cells. For example, these cells can be extracted from whole blood using ficoll, a hydrophilic polysaccharide that separates layers of blood, and gradient centrifugation, which will separate the blood into a top layer of plasma, followed by a layer of PBMCs and a bottom fraction of polymorphonuclear cells (such as neutrophils and eosinophils) and erythrocytes. The polymorphonuclear cells can be further isolated by lysing the red blood cells. Basophils are sometimes found in both the denser and the PBMC fractions.

Specifically, the host of the non-human mammalian model of the invention is engrafted with human peripheral blood lymphocytes alone or in combination with donor-matched monocyte-derived dendritic cells. Mice engrafted with both human peripheral blood lymphocytes and monocyte-derived dendritic cells demonstrate antigen-specific T cell proliferation and cytokine production.

The cells constituting the huSE and the engrafted immune cells can be derived from the same human donor (autologous) or from different donors (allogeneic). Depending on the type of application the model is to be used for, autologous or allogeneic donors are required. For example, models for the study of autoimmune diseases regularly require autologous donors. The advantage of allogeneic donors is, for example, easier generation of the huSE as readily prepared cell slurries of fibroblasts and keratinocytes can be used.

In a preferred embodiment, the method of generating the non-human mammalian model comprises the steps of in vitro expanding skin cells, preferably keratinocytes and fibroblasts, provided by a human donor, to generate a human skin equivalent, which is then engrafted onto a non-human mammalian host and which host is further engrafted with human immune cells, harvested from the same or different human donor. Furthermore, the non-human mammalian is depleted of neutrophils. As skin cells are expanded in vitro prior to engraftment using silicone chambers, less patient material is required and cells can be manipulated prior to engraftment. Specifically, cells can be manipulated by genetic modification as described above.

Specifically, the cell slurry used for engraftment of the huSE comprises at least $1\times10^5$, $5\times10^5$, $1\times10^6$, $1.5\times10^6$, $2\times10^6$, $2.5\times10^6$, $3\times10^6$, $5\times10^6$ or $1\times10^7$ primary or immortalized human keratinocytes and at least $1\times10^5$, $5\times10^5$, $1\times10^6$, $1.5\times10^6$, $2\times10^6$, $2.5\times10^6$, $3\times10^6$, $5\times10^6$ or $1\times10^7$ primary or immortalized human fibroblasts. Preferably, at least $2.5\times10^6$, and even more preferably $1\times10^6$ primary or immortalized human keratinocytes and at least $2.5\times10^6$, and even more preferably $1\times10^6$ primary or immortalized human fibroblasts are comprised in the cell slurry.

In a further embodiment, the cell slurry used for engraftment of the huSE comprises further cell types in addition to keratinocytes and fibroblasts. Specifically, these further cell types are skin cells such as melanocytes, Merkel cells, Langerhans cells or skin stem cells, specifically epidermal and dermal stem cells.

According to a specific embodiment of the method provided herein, the non-human mammalian host is engrafted with at least $1\times10^5$, $0.5\times10^6$, $1\times10^6$, $5\times10^6$ or $1\times10^7$ human immune cells, selected from the group consisting of T cells, B cells, natural killer cells, monocytes, monocyte derived dendritic cells, dendritic cells and their subtypes, tissue-derived dendritic cells, Langerhans cells, γδ-T cells, mast cells, innate lymphoid cells (ILC), and human peripheral blood mononuclear cells (huPBMC). Preferably, the non-human mammalian host is engrafted with at least $1\times10^6$, preferably $5\times10^6$, and even more preferably $3\times10^6$ immune cells. Using at least $3\times10^6$ immune cells results in stable engraftment and significantly delayed expansion of $CD8^+$ T cells and graft-versus-host-disease. However, after transfer of $5\times10^6$ immune cells, the ratio between $CD4^+$ and $CD8^+$ remains stable for approximately 4 to 5 weeks. Injection of $1\times10^6$ immune cells leads to engraftment without the development of xeno-graft-versus-host-disease for several months, which leaves ample time to perform functional experiments.

Specifically, the non-human mammalian host is engrafted with only one type of human immune cells or with multiple types of human immune cells.

In a preferred embodiment, human immune cells are isolated from human donor blood. Preferably, the human immune cells are frozen in an aqueous solution after isolation. Specifically, the immune cells are frozen using liquid nitrogen in media comprising serum and DMSO. Preferably, the immune cells are thawed overnight for at least 18 hours at 37° C. in resting media prior to transfer to the model host. Said resting media can be any physiological solution suitable for the cell culture of mammalian cells, especially human cells. Defined cell culture media are based on the component groups amino acids, carbohydrates, inorganic salts and vitamins. Frequently included salts are calcium chloride, potassium chloride, magnesium sulfate, sodium chloride and monosodium phosphate. Frequently contained vitamins are folic acid, nicotinamide, riboflavin and B12. In addition, the cell culture medium may contain FCS (Fetal Calf Serum) or FBS (Fetal Bovine Serum). Preferred cell culture media are MEM, α-MEM, DMEM, RPMI and variations or modifications thereof. Preferably said resting media is RPMI-1640. Preferably said resting media further comprises human serum, L-glutamine, pen/strep, sodium pyruvate, and non-essential amino acids (NEAA). Specifically, said resting media is RPMI-1640 comprising 5% human serum, 1% L-glutamine, 1% pen/strep, 1% sodium pyruvate, and 1% non-essential amino acids (NEAA). Such procedure has the advantage that donor samples can be stored for prolonged time periods.

Presented herein is a novel and unique skin-humanized non-human mammalian model to study T cell responses against a specific skin antigen. The model is unique in its usage of a target tissue that is absolutely devoid of resident immune cells. Primary human skin tissue that is free of any immune cells cannot be obtained from healthy donors, particularly not from adult donors. The model of the invention therefore allows the analysis and manipulation of skin-tropic T cells without the impact of already resident T cells within the tissue. Importantly, the inventors' data shows that the T cells that migrate to the huSE within the humanized model are remarkably similar to T cells within primary human skin. This similarity in phenotype shows that the tissue imprints a certain phenotype in the T cells and/or stabilizes phenotypes best suited to support its homeostatic functions.

The model of the invention further allows the analysis of antigen-specific immune responses in vivo which was previously not possible with any available humanized models. Humanized mouse models that could support antigen-specific responses are based on the engraftment of fetal tissues (bone-marrow, liver, thymus [BLT] mouse), which obviously does not allow the study of patient material obtained from adults. Only indirect methods (such as ex vivo restimulation with antigen-loaded dendritic cells) or serum cytokine levels (which do not allow to determine the cell source) could be used to define the in vivo response. No available model allows researchers to study the role of individual, specific immune cell types within the skin tissue or the interaction of select immune cells within the skin tissue. The model provided herein can overcome the limitations of currently available models by introducing a target tissue that supports normal immune responses in the absence of a (local) xeno-response usually observed within humanized non-human mammalian models.

The non-human mammalian model provided herein can be used as an animal model for skin related diseases or disorders. Specifically, the model provided herein is used to study T cell responses against a specific skin antigen and the model is specifically suited to study the contribution of individual cell types (e.g. keratinocytes, fibroblasts, innate or adaptive immune cells) to skin responses. Preferably, the model provided herein is used for the study of immune-mediated skin diseases, including skin related autoimmune diseases and allograft rejection, genodermatoses or malignant diseases.

Specifically, the immune-mediated skin disease can be dermatitis, vitiligo, mastocytosis or lupus. Specifically, the immune-mediated skin disease can further be an autoimmune disease, such as scleroderma, psoriasis, dermatomyositis, epidermolysis bullosa, and bullous pemphigoid and allergic reactions.

Specifically, the genodermatosis can be epidermolysis bullosa, ichthyosis, palmoplantar keratoderma, neurofibromatosis, xeroderma pigmentosum, incontinentia pigmenti, restricitive dermopathy or pachyonychia congenital.

Specifically, the malignant skin disease can be basal cell carcinoma, squamous cell carcinoma, melanoma, Merkel cell carcinoma, sarcoma, cutaneous skin lymphoma or skin adnexal tumors.

According to a further embodiment of the invention the non-human mammalian model provided herein is used for the study of skin resident immune cells in barrier function of the skin, for the study of skin resident immune cells in wound healing or for the study of skin resident immune cells in cancer clearance.

According to a further embodiment of the invention the non-human mammalian model provided herein is used for the study of the response to foreign therapeutic skin-antigens of individual patients prior to a planned therapy. Such therapies include for example skin gene therapy of monogenetic skin diseases, RNA therapies, protein therapy or cell therapy.

According to a further embodiment of the invention the non-human mammalian model provided herein is used for the study of the mechanism, function or efficacy of immunomodulatory drugs in skin diseases.

According to a further embodiment of the invention the non-human mammalian model provided herein is used for the study of hair follicle biology and hair follicle development. Specifically, it is used for the study of the interaction between hair follicle cells and immune cells.

According to a further embodiment of the invention the non-human mammalian model provided herein is used for studying pharmaceuticals, cell products, biologics or small molecules targeting skin cells, or delivery systems such as nanoparticles, microbubbles, microneedles or gene guns.

EXAMPLES

The Examples which follow are set forth to aid in the understanding of the invention but are not intended to, and should not be construed to limit the scope of the invention in any way. The Examples do not include detailed descriptions of conventional methods. Such methods are well known to those of ordinary skill in the art.

In order to achieve humanized mouse models researchers have developed highly immunodeficient recipient strains such as the state of the art NSG (NOD Scid common-γ chain$^{-/-}$) mouse (1) (2). NSG mice lack mature T cells, B cells, and natural killer (NK) cells and, in addition, they have many defects in innate immunity (3). Among the various humanized mouse models (4) we chose an established approach that is best suited to analyze immune cells from adult patients (FIG. 1): Adoptive transfer of human peripheral blood mononuclear cells (huPBMC) into NSG mice (5). This huPBMC-model is easy to establish, shows strong T cell engraftment and studies can commence immediately after adoptive transfer (6). Injection of 1-5×10$^6$ Ficoll-purified PBMC leads to engraftment without the development of xeno-graft-versus-host disease (GVHD) for several months (7), which leaves ample time to perform any functional experiments. In addition to the adoptive transfer of PBMCs we graft the mice with organotypic skin equivalents (SE) from the same donor that donated the PBMC. Obviously, it is also possible to perform similar experiments with an allogeneic donor. These SE are generated from isolated keratinocytes and fibroblasts, using a technique similar to our previously described approach (8).

Hereinafter we demonstrate full establishment of the two main parts of the model system (i.e. human skin and lymphoid compartment).

Example 1

Engineered Human Skin Devoid of Any Immune Cells can be Generated on NSG Mice

Figure 2:
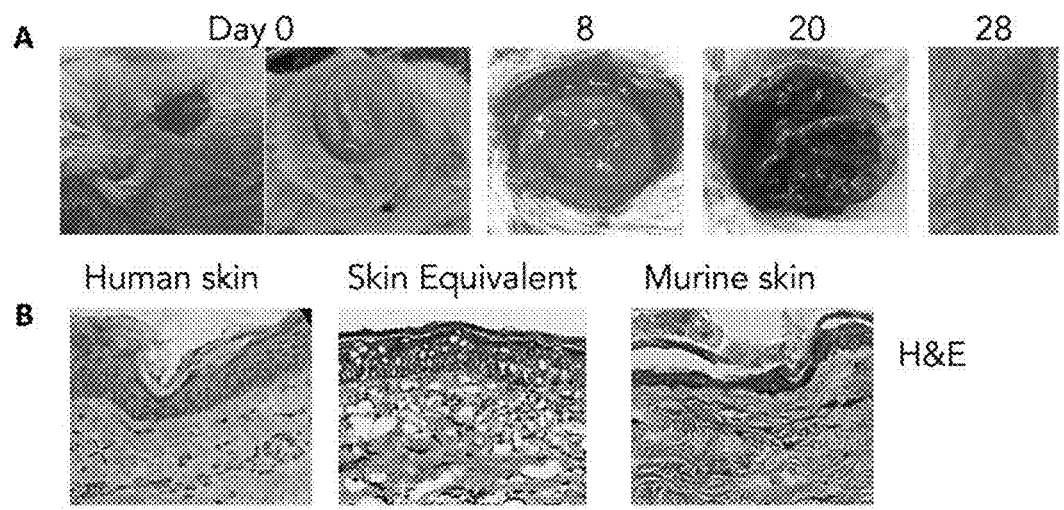
FIG. 2 depicts the generation of human skin equivalents on immunodeficient NSG mice. (A) Surgical procedure of placing silicone skin grafting chambers on the backs of NSG mice (day 0). $2.5 \times 10^6$ in vitro expanded immortalized human keratinocytes and $2.5 \times 10^6$ human fibroblasts (from a healthy donor) are added to the chamber and left without movement to settle and self-sort for approx. 45 min (during which the mice are kept under full anesthesia). The chambers are removed after seven days and the human skin left to develop and differentiate. Appearance of human skin equivalent (SE) on day 8, 20 (scab formation) and 28 (fully healed) post grafting. (B) Histological appearance of full thickness human skin, SE and murine skin stained with hematoxylin and eosin (H&E).

Rather than grafting 3D-skin cultures similar to previously reported studies (9) it was found that the use of grafting chambers is an easier approach to provide comparable skin generation. The use of grafting chambers was established to create human skin equivalents on NSG mice similar to a previously reported approach (8). In this approach either primary or immortalized keratinocytes and fibroblasts were expanded in vitro and then place a 1:1-mix of both cell types in silicone chambers on the back of recipient mice. These cells then sort spontaneously and differentiate into skin tissue (FIG. 2A).

For the surgical procedure silicone skin grafting chambers were implanted on the backs of NSG mice (day 0). $2.5 \times 10^6$ in vitro expanded immortalized human keratinocytes and $2.5 \times 10^6$ human fibroblasts (from a healthy donor) were added to the chamber and left without movement to settle and self-sort for approx. 45 min (during which the mice are kept under full anesthesia). The chambers were removed after seven days and the human skin left to develop and differentiate. Histological H&E images of human skin equivalent (SE) on days 8, 20 (scab formation) and 28 (fully healed) showed full thickness human skin. C7 was expressed in the basal membrane zone of human control skin as well as in the human skin equivalents but not in murine control skin.

It was found that in addition to using primary cells from healthy donors also immortalized primary keratinocytes (using a viral E6/E7 system (10)) derived from either patients and healthy donors (HD) could be used to produce skin tissue from immortalized keratinocytes and primary or immortalized fibroblasts. In order to confirm the correct differentiation and human origin H&E staining was performed and it was found that the epidermis of the SE is multi-layered which is typical of human but not surrounding murine skin (FIG. 2B). In order to confirm correct self-sorting of the cells they were also stained for correct deposition of type VII collagen (C7). It was found that the majority of C7 was deposited at the basement membrane zone at the dermal-epidermal junction similar to normal full thickness skin. Together with the H&E data, this suggests correct self-sorting of the cells, as well as correct differentiation.

Example 2

Adoptively Transferred Human T Cells Engraft in NSG Mice

A model was successfully established, designated huPBMC-NSG, in which human PBMC were isolated from blood and transferred to NSG mice. By resting the PBMC overnight in resting media prior to transfer, a method to reproducibly engraft recipient mice using frozen PBMC was established, which is crucial for this kind of study for which use of biobanked patient material is ultimately intended.

Despite the fact that NSG mice are highly immunodeficient, they still produce a viable granulocyte/neutrophil population that can mediate some degree of host-versus-graft-disease leading to the rejection and poor engraftment of human PBMC. In order to minimize this response neutrophils were depleted using an anti-granulocyte receptor-1 (Gr-1) monoclonal antibody (mAb clone RB6-8C5) (11). For that 100 μg/mouse were injected starting on the day of PBMC-injection followed by mAb-injections every 5-6 days. It was found that CD4+ and CD8+ T cells are the main immune cell type that engrafts (typically>95% of all human CD45+ leukocytes) (FIG. 3A) while B cell engraftment is almost undetectable (not shown, previously reported for huPBMC mice (12)).

Figure 3:
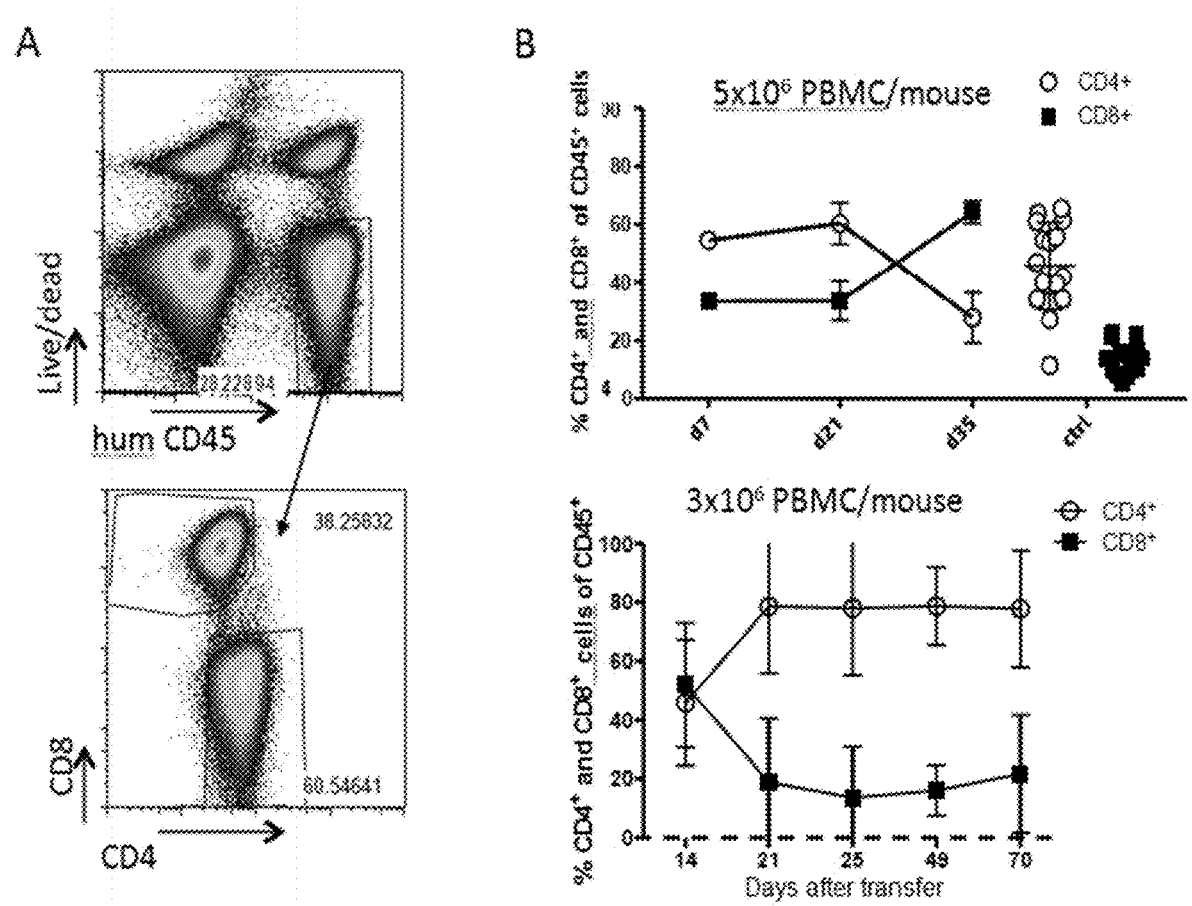
FIG. 3 depicts engraftment of PBMC in immunodeficient NSG mice. PBMC from a healthy donor were thawed and rested for 18 hours before transfer of $3 \times 10^6$ or $5 \times 10^6$ PBMC/mouse by i.v. injection. (A) Representative FACS plots of human immune cells (pre-gated on live CD45+ cells) found in NSG spleens. (B) We analyzed the percentage of CD4+ and CD8+ of all human immune cells (pre-gated on live CD45+ cells) at the indicated time points after PBMC transfer. N=4 mice; Ctrl: fresh donor PBMC.
Figure 7:
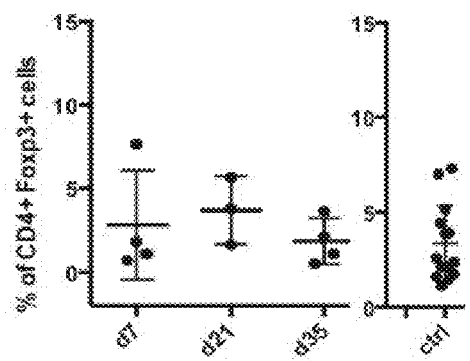
FIG. 7 depicts phenotypic analysis of the regulatory T cell compartment. Splenocytes were isolated from NSG recipient mice 7-35 days after adoptive transfer of $5 \times 10^6$ PBMC/mouse and analyzed by flow cytometry using antibodies against human CD45, CD4, CD25 and Foxp3. The plot shows the percentage of Foxp3+ Treg of the CD4+ population. Ctrl: healthy donor PBMC (prior to transfer).

Transfer of human PBMC into NSG is known to eventually result in xeno-graft-versus-host disease (GvHD), which is accompanied by an inflammatory skin reaction mediated by an expanded CD8+ T cell population (i.e. a shift in the ratio of CD4+:CD8+ T cells). Since this xeno-GvHD would confound the findings concerning anti-skin graft reactions the inventors sought to define a window of experimentation (i.e. the time before the onset of cellular changes related to GvHD). It was found that after transfer of $5 \times 10^6$ PBMC the ratio between CD4+ and CD8+ T cells remained stable (at a ratio resembling the ingoing PBMC) for approx. 4-5 weeks. Interestingly, regulatory T cells, a CD4 T helper subtype, were preserved during this time (FIG. 7). After this time the ratio changed and CD8+ T cells selectively expanded (FIG. 3B), which coincided with the onset of mild clinical signs of GvHD. Importantly, it was found that a reduction of the transferred cell number to $3 \times 10^6$ PBMC still resulted in stable engraftment but significantly delayed expansion of CD8+ T cells and GvHD (FIG. 3B). Based on these data it was concluded that the experiments in which $5 \times 10^6$ PBMC/mouse are transferred should ideally have a maximum length of approximately 4 weeks after PBMC transfer. By contrast, experiments in which $2-3 \times 10^6$ PBMC/mouse are transferred could have a maximum length of approximately up to 10 weeks after PBMC transfer.

Remarkably, when the same system was tested in an allogeneic skin grafting setting, full clinical graft rejection in this skin-humanized mouse model could not be observed. This is in line with data from other groups using low PBMC numbers in a similar model (15).

Example 3

T Cells Migrate to Human SE in Skin-Humanized Mice

Figure 4:
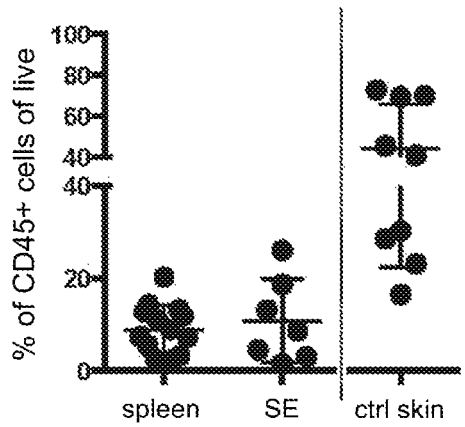
FIG. 4 depicts engraftment of human leukocytes in human SE on immunodeficient NSG mice. $2.5 \times 10^6$ in vitro expanded immortalized human keratinocytes and $2.5 \times 10^6$ human fibroblasts (from a healthy donor) were grafted as described in FIG. 2 and Example 1. 35 days after grafting (after healing of the SE) PBMC from a healthy donor were thawed and rested for 18 hours before transfer of $3 \times 10^6$ PBMC/mouse by i.v. injection (as in FIG. 3). 30 days after transfer single cell suspensions were prepared from spleen and SE, and cells were subjected to flow-cytometric analysis. (A) Percentage of live CD45+ cells found in NSG spleens or SE. (B) The percentage of CD4+ and CD8+ of all human immune cells was analyzed (pre-gated on live CD45+ cells). (C) Engraftment of HLA-DR+ CD3- (pre-gated on live CD45+ cells) cells in the designated tissues. N=7 mice; Ctrl skin: fresh skin from healthy donors (discarded during plastic/reconstructive surgery).
Figure 4:
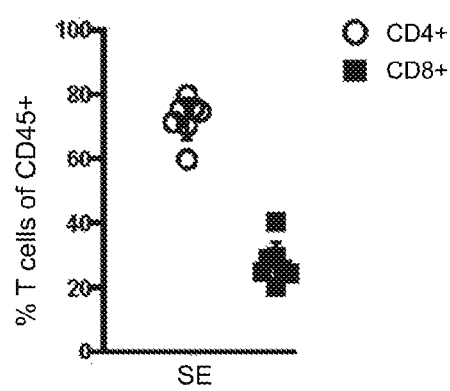
Figure 4:
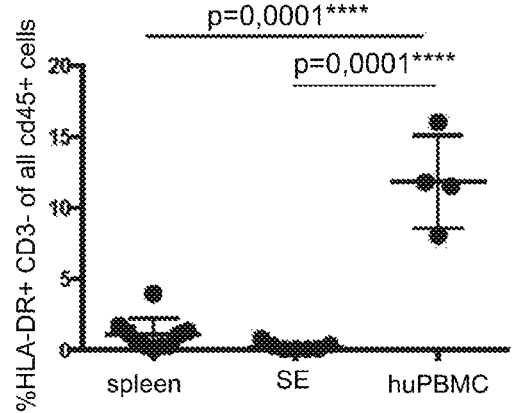

Next it was aimed to determine whether human T cells would engraft in the human SE. To this end, NSG mice were grafted with human SE and injected (i.v.) with autologous human PBMC after the SE had fully healed. After 3 weeks the spleen and SE were analyzed by flow cytometry and it was found that the human T cells did in fact migrate to the SE (FIG. 4A) and that the ratio of CD4:CD8 cells was preserved at an approximate ratio of 4:1 as found in healthy donors (FIG. 4B).

Example 4

Antigen-Presenting Cells Engraft Poorly and Do Not Migrate to Human SE

In contrast to T cells it was found that antigen-presenting cells (APC) engraft at low percentages compared to the ingoing PBMC (FIG. 4C). This is in accordance with previous reports that showed that not all lineages of immune cells engraft equally efficiently upon adoptive transfer of human PBMCs. Importantly, the poor engraftment of human APC in the huPBMC model is known to hamper primary immune responses in current models. However, low numbers of human APC are detectable in multiple tissues such as spleen (FIG. 4C) and lung in huPBMC humanized mice (13) and they can potentially even be recruited to the skin under certain conditions (14). However, little engraftment of APC within the SE was detected under the present conditions (i.e. healed/homeostatic conditions and untreated SE).

Example 5

T Cells Within Human SE Display a Skin Typical Cytokine Profile

Figure 5:
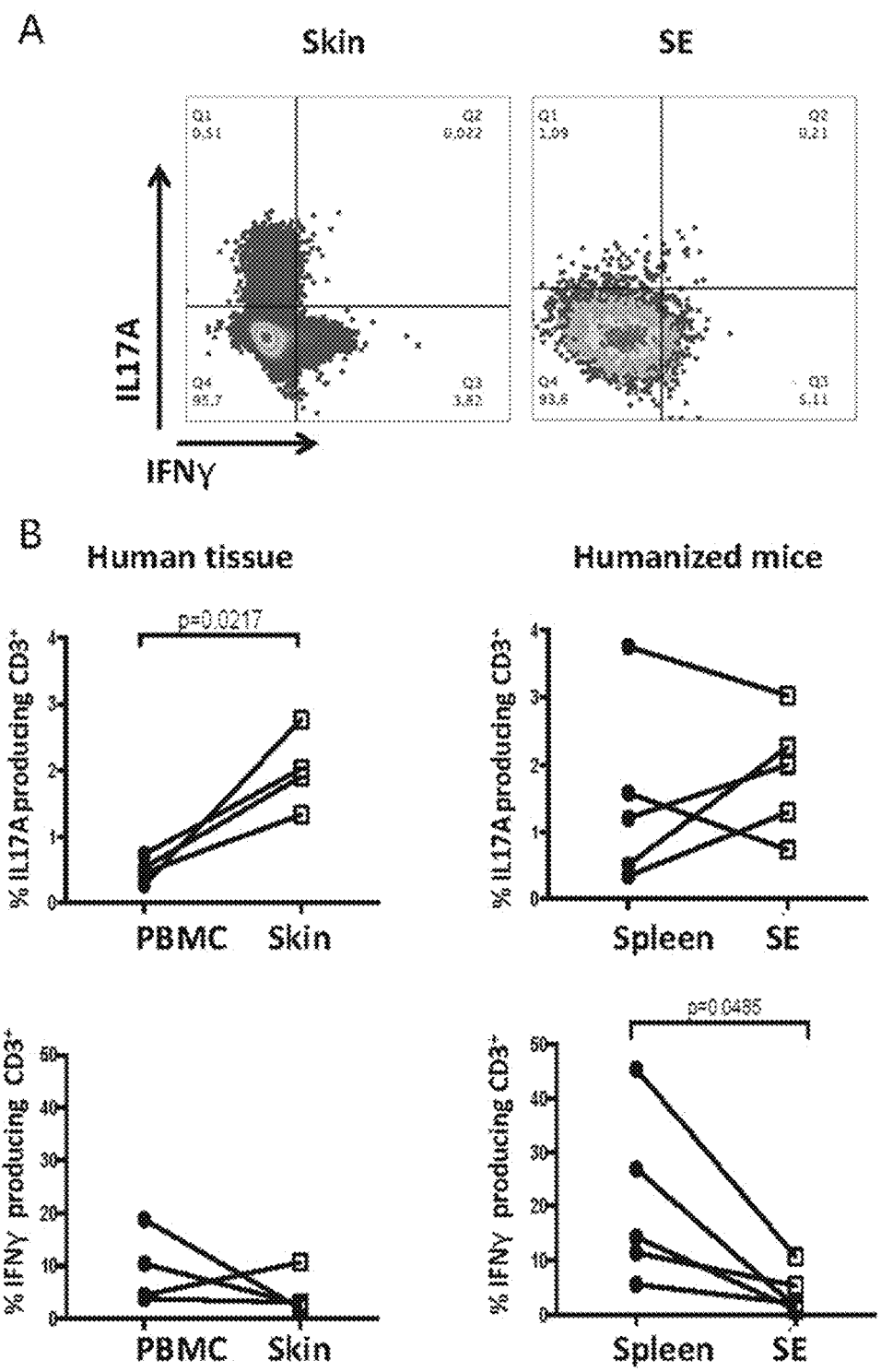
FIG. 5 depicts comparable cytokine profiles between human skin and SE of skin-humanized mice. As for FIG. 4, $2.5 \times 10^6$ in vitro expanded immortalized human keratinocytes and $2.5 \times 10^6$ human fibroblasts (from a healthy donor) were grafted as described in FIG. 2 and Example 1. 35 days after grafting (after healing of the SE) PBMC from a healthy donor were thawed and rested for 18 hours before transfer of $3 \times 10^6$ PBMC/mouse by i.v. injection (as in FIG. 3). 30 days after transfer we prepared single cell suspensions from spleen and SE, and stimulated the cells with PMA/ionomycin in the presence of Brefeldin A. Intracellular cytokine production was then determined by flow-cytometric analysis. (A and C) Representative FACS plot of the designated intracellular cytokines pre-gated on live CD45+CD3+ T cells. (B) The percentage of the respective cytokines within CD3+ T cells in the designated tissues. Each dot represents one mouse or one healthy donor; Human tissue: PBMC and matched fresh skin from healthy donors (discarded during plastic/reconstructive surgery).
Figure 5:
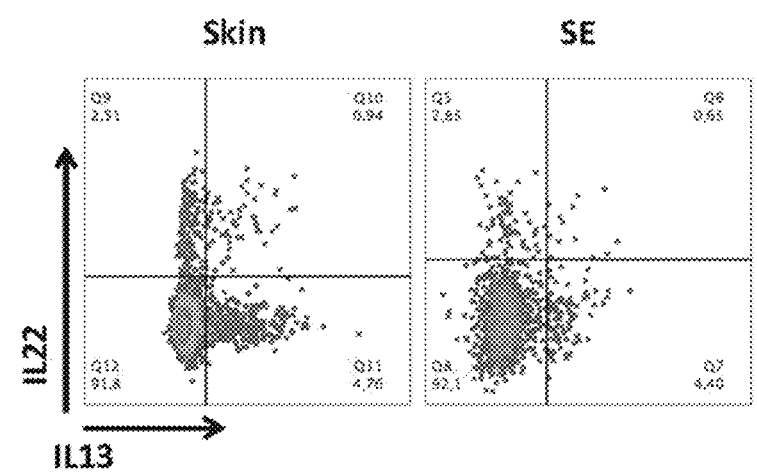
Figure 5:
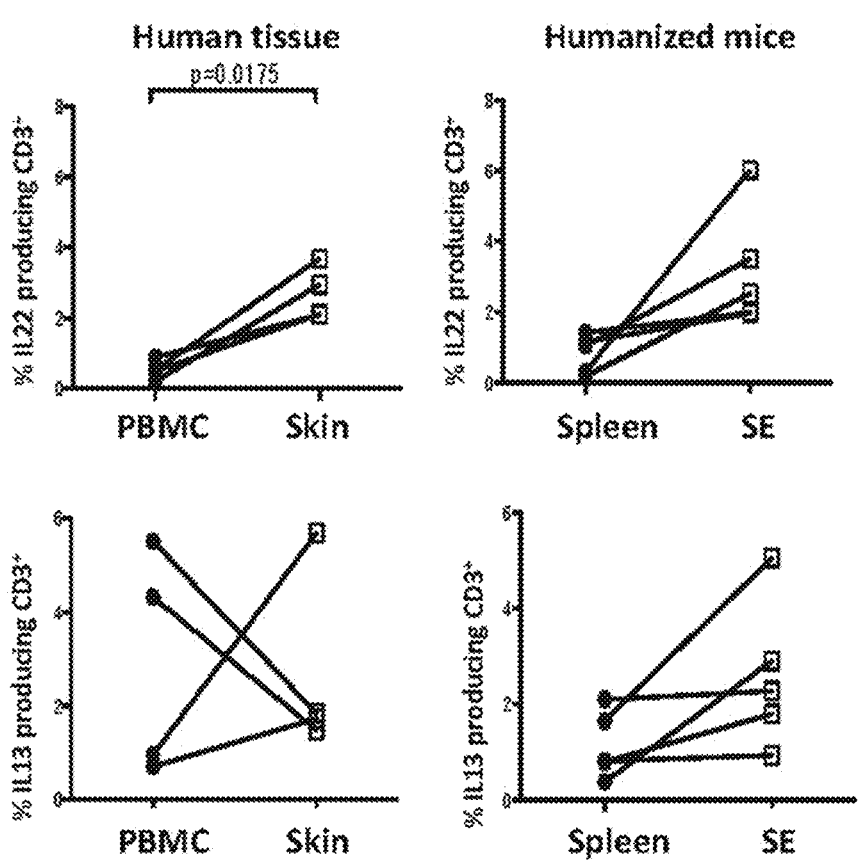

It was then intended to determine whether T cells that engraft in the SE have a phenotype comparable to healthy skin. The preservation of the cytokine phenotype was considered a prerequisite to the development of a humanized mouse model to study skin T cell responses. To test this, T cells were isolated from SE and spleens of skin-humanized mice (as for FIG. 4) and stimulated ex vivo to determine their cytokine profiles. These were then compared with PBMC and fresh full-thickness skin from healthy donors (FIG. 5). It was found that cytokine production was somewhat elevated within the spleen compared to PBMC but remarkably preserved between healthy skin tissue and SE. This finding suggests that the human tissue normalizes the phenotype of human T cells that seem to display a slight xeno-reactivity within the murine spleen.

Example 6

Figure 8:
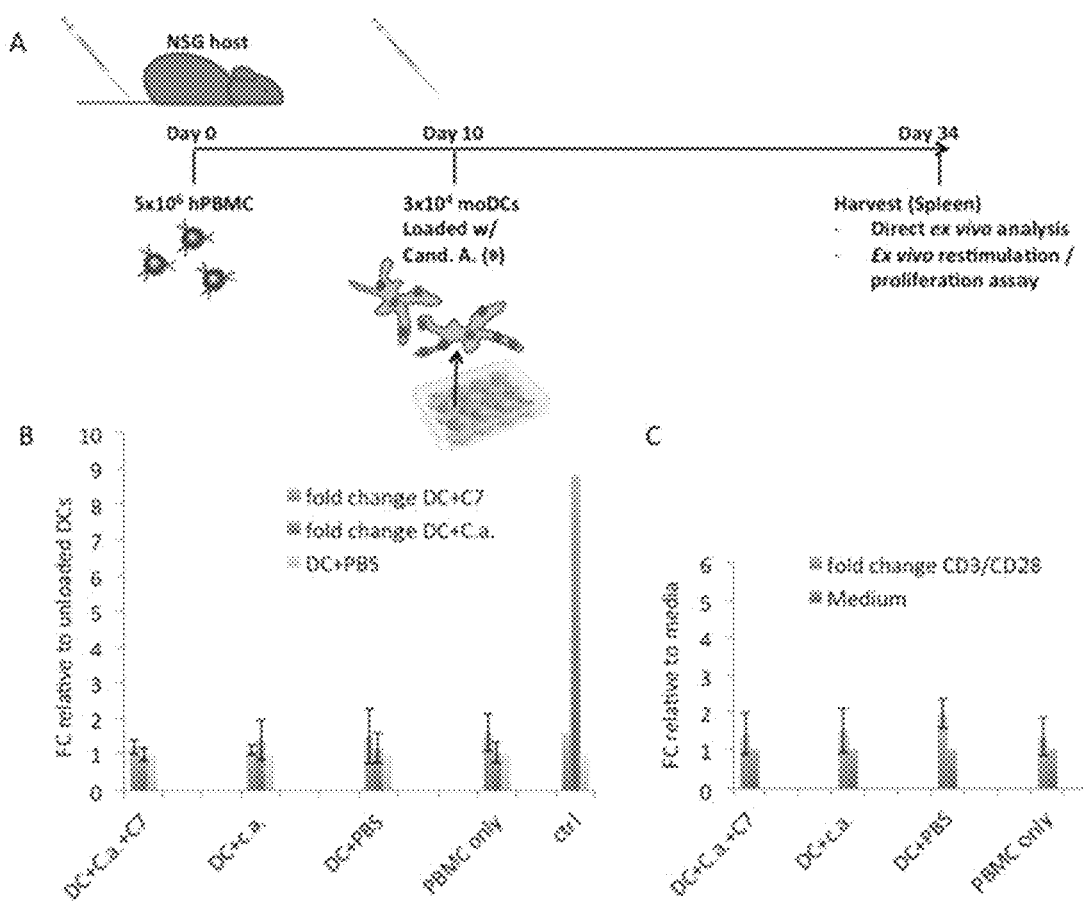
FIG. 8 shows that antigen-loaded moDC do not expand C7-specific T cells in NSG mice. (A) Experimental setup: $5 \times 10^6$ PBMC were transferred into recipient mice and the APC population subsequently supplemented with $3 \times 10^4$ monocyte-derived dendritic cells (moDC) from the same (autologous) healthy donor. (B) Splenocytes were stimulated with antigen-loaded moDC+IL2 (C) or with anti-CD3/anti-CD28 stimulating antibodies+IL2. The x-axis designates the moDC population applied in vivo and the legend designates the moDC-population used for ex vivo re-stimulation. As stimulation control (ctrl) we included primary PBMC of the same donor directly stimulated ex vivo. N=3/group.

Human T Cells Respond to Skin Antigen Presented in Skin but Not to Systemic Antigen Since it was aimed to detect and follow T cells during an immune response against skin antigens, their response to known skin antigens was tested. A known strong antigen was used against which almost every individual has pre-existing immunity, *Candida albicans* (*Cand.a.*). Importantly, *Cand.a.* is also a common wound colonizer in people with chronic wounds. Based on the low engraftment of antigen-presenting cells (APC) (FIG. 4C) it was hypothesized and found that T cell responses would not be induced efficiently without addition of APC. Mature human APC can also be generated in vitro from PBMCs in the presence of GM-CSF and IL-4 and transferred into the mice. This procedure has previously been shown to significantly improve priming of primary immune responses (13). Therefore, autologous monocyte-derived dendritic cells (moDCs) from PBMC were generated in vitro using IL-4 and GM-CSF as APCs and they were loaded in vitro with heat-killed *Cand.a.* antigen. These *Cand.a.*-loaded moDCs were then injected intravenously (i.v.) into NSG recipients together with the PBMC. Two weeks after transfer splenocytes were isolated and the cells restimulated with moDC+ *Cand.a.* in vitro. This restimulation did not result in significant ex vivo proliferation (FIG. 8). It was concluded that i.v. injection results in poor T cell stimulation and poor expansion of antigen-specific T cells.

Figure 6:
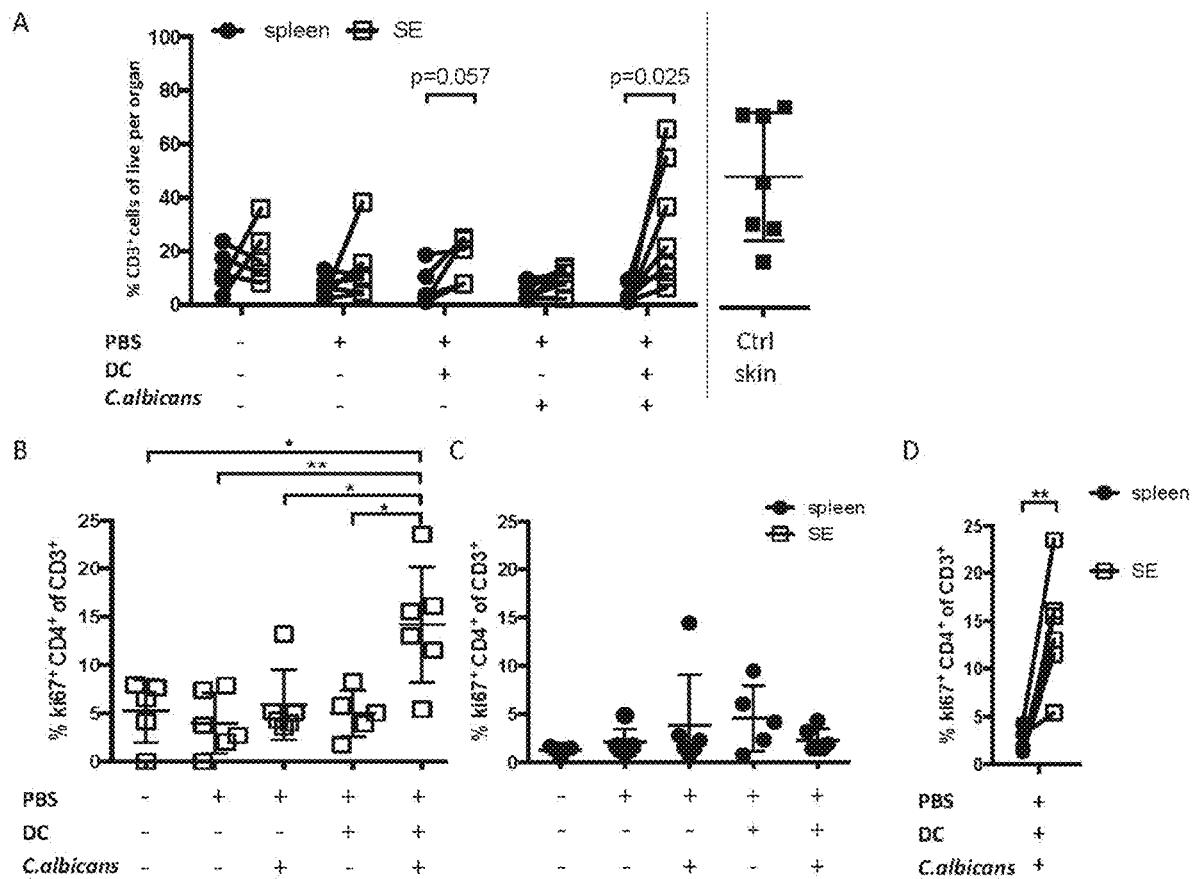
FIG. 6 depicts T cell response to skin antigen in humanized NSG mice. SE were generated from keratinocytes and fibroblasts of a healthy donor on the backs of NSG recipients as described in FIG. 2 and Example 1. 28 days after SE grafting $3 \times 10^6$ autologous PBMC/mouse were injected i.v. 21 days after PBMC injection the SE were injected with PBS, heat-killed Cand.a., LPS-activated moDC (DC) or moDC loaded with heat-killed Cand.a. i.d. three times within a week and SE, spleen and murine skin were harvested 7 days after the last injection. (A) Single cell suspensions of SE and spleen were prepared 7 days after treatment ended and the percentage of CD45+ human immune cells in SE and fresh full-thickness skin analyzed by FACS. (B,C) Same as (A) but CD3+ T cells analyzed for their expression of the proliferation marker Ki67 in the SE (B) and the spleen (C). (D) same as (A) but spleen and SE are shown side by side.
Figure 9:
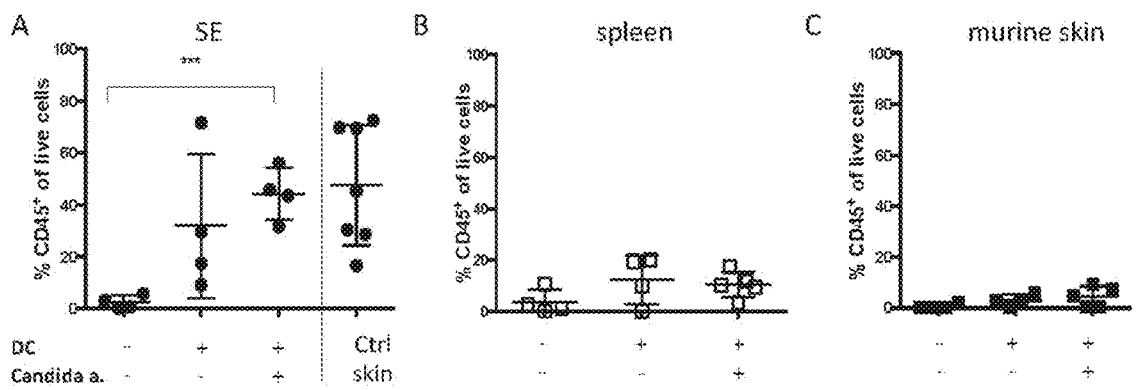
FIG. 9 depicts recruitment of immune cells to human SE but not murine skin of humanized NSG mice. SE were generated from keratinocytes and fibroblasts of a healthy donor on the backs of NSG recipients. 28 days after SE grafting $3 \times 10^6$ autologous PBMC/mouse were injected i.v. 21 days after PBMC injection LPS-activated moDC or moDC loaded with heat-killed Cand.a. were injected i.d. three times within a week and SE, spleen and murine skin were harvested 7 days after the last injection. (A) The percentage of CD45+ human immune cells in SE and fresh full-thickness skin was analyzed. (B, C) same as (A) but spleen and murine skin are shown.

Based on these data it was hypothesized that a specific T cell response to a skin antigen would be more vigorous and also enriched for skin-antigen-specific T cells if the antigen was presented locally in the skin tissue (i.e. the usual site of infection). In order to test this, NSG mice were grafted with human SE and autologous human PBMC were injected (i.v.) after the SE had fully healed. Then, either unloaded moDC or moDC loaded with *Cand.a.* antigen were injected intradermally (i.d.) into the SE and it was found that i.d. injection of moDC increased infiltration of the SE by T cells but did not result in a systemic expansion (FIG. 6A). Also, no unspecific infiltration of murine skin (FIG. 9) was observed. Importantly, by intracellular staining of the proliferation marker Ki67 it was observed that *Cand.a.* antigen induced specific proliferation within the SE (FIG. 6B) but not systemically (FIGS. 6C and D). These data suggest that T cells recognize antigen locally within the skin and proliferate locally but not systemically. Importantly, this response requires antigen-presenting cells within the skin tissue.

These data suggest that skin-specific responses are most vigorous locally within the target tissue. This might be especially true in a situation where memory T cells already have a skin-homing phenotype imprinted like it is the case with *Cand.a.*-specific responses (16).

A novel and unique model to study T cell responses against a specific skin antigen was developed by the inventors. The model is unique in its usage of a target tissue that is absolutely devoid of resident immune cells. Primary human skin tissue that is free of any immune cells cannot be obtained from healthy donors, particularly not from adult donors (17). This allows the analysis and manipulation of skin-tropic T cells without the impact of already resident T cells within the tissue. Importantly, our data indicate that the T cells that migrate to the SE within the humanized mouse model are remarkably similar to T cells within primary human skin. This similarity in phenotype suggests that the tissue imprints a certain phenotype in the T cells and/or stabilizes phenotypes best suited to support its homeostatic functions.

The inventive model further allows the analysis of antigen-specific immune responses in vivo which was not possible with any available humanized mouse models. Humanized mouse models that could support antigen-specific responses are based on the engraftment of fetal tissues (bone-marrow, liver, thymus [BLT] mouse (18)), which obviously does not allow the study of patient material obtained from adults. Alternatively, the engraftment of moDC similar to our approach was used to allow/augment antigen-specific immune responses (19). However, in this model high numbers of PBMC ($10 \times 10^6$) were required and the direct detection of responding T cells was technically very challenging, presumably due to the very low frequency of responding T cells within the spleen. Thus, mainly indirect methods (such as ex vivo restimulation with antigen-loaded dendritic cells) or serum cytokine levels (which do not allow to determine the cell source) could be used to define the in vivo response.

Thus, the inventive model overcomes the limitations of currently available models and thus fills an apparent gap in the field and solves major shortcomings of current models. This is achieved by introducing a target tissue that supports normal immune responses in the absence of a (local) xeno-response usually observed within humanized mice. The novel model thus offers clear advantages over the known models.

REFERENCES

1. Shultz, L. D., F. Ishikawa, and D. L. Greiner. 2007. Humanized mice in translational biomedical research. *Nat. Rev. Immunol.* 7: 118-130.

2. Garcia, S., and A. A. Freitas. 2012. Humanized mice: current states and perspectives. *Immunol. Lett.* 146: 1-7.
3. Shultz, L. D., B. L. Lyons, L. M. Burzenski, B. Gott, X. Chen, S. Chaleff, M. Kotb, S. D. Gillies, M. King, J. Mangada, D. L. Greiner, and R. Handgretinger. 2005. Human lymphoid and myeloid cell development in NOD/LtSz-scid IL2R gamma null mice engrafted with mobilized human hemopoietic stem cells. *J. Immunol. Baltim. Md.* 1950174: 6477-6489.
4. Shultz, L. D., M. A. Brehm, J. V. Garcia-Martinez, and D. L. Greiner. 2012. Humanized mice for immune system investigation: progress, promise and challenges. *Nat. Rev. Immunol.* 12: 786-798.
5. King, M., T. Pearson, L. D. Shultz, J. Leif, R. Bottino, M. Trucco, M. A. Atkinson, C. Wasserfall, K. C. Herold, R. T. Woodland, M. R. Schmidt, B. A. Woda, M. J. Thompson, A. Rossini, and D. L. Greiner. 2008. A new Hu-PBL model for the study of human islet alloreactivity based on NOD-scid mice bearing a targeted mutation in the IL-2 receptor gamma chain gene. *Clin. Immunol. Orlando Fla.* 126: 303-314.
6. Pearson, T., D. L. Greiner, and L. D. Shultz. 2008. Creation of "humanized" mice to study human immunity. *Curr. Protoc. Immunol. Ed. John E Coligan Al* Chapter 15: Unit 15.21.
7. Pino, S., M. A. Brehm, L. Covassin-Barberis, M. King, B. Gott, T. H. Chase, J. Wagner, L. Burzenski, O. Foreman, D. L. Greiner, and L. D. Shultz. 2010. Development of novel major histocompatibility complex class I and class II-deficient NOD-SCID IL2R gamma chain knockout mice for modeling human xenogeneic graft-versus-host disease. *Methods Mol. Biol. Clifton NJ*602: 105-117.
8. Wang, C. K., C. F. Nelson, A. M. Brinkman, A. C. Miller, and W. K. Hoeffler. 2000. Spontaneous cell sorting of fibroblasts and keratinocytes creates an organotypic human skin equivalent. *J. Invest. Dermatol.* 114: 674-680.
9. Carretero, M., S. Guerrero-Aspizua, N. Illera, V. Galvez, M. Navarro, F. Garcia-Garcia, J. Dopazo, J. L. Jorcano, F. Larcher, and M. del Rio. 2016. Differential Features between Chronic Skin Inflammatory Diseases Revealed in Skin-Humanized Psoriasis and Atopic Dermatitis Mouse Models. *J. Invest. Dermatol.* 136: 136-145.
10. Merkley, M. A., E. Hildebrandt, R. H. Podolsky, H. Arnouk, D. G. Ferris, W. S. Dynan, and H. Stoppler. 2009. Large-scale analysis of protein expression changes in human keratinocytes immortalized by human papilloma virus type 16 E6 and E7 oncogenes. *Proteome Sci.* 7: 29.
11. Daley, J. M., A. A. Thomay, M. D. Connolly, J. S. Reichner, and J. E. Albina. 2008. Use of Ly6G-specific monoclonal antibody to deplete neutrophils in mice. *J. Leukoc. Biol.* 83: 64-70.
12. Smithson, S. L., N. Srivastava, W. A. Hutchins, and M. A. Westerink. 1999. Molecular analysis of the heavy chain of antibodies that recognize the capsular polysaccharide of Neisseria meningitidis in hu-PBMC reconstituted SCID mice and in the immunized human donor. *Mol. Immunol.* 36: 113-124.
13. Hammad, H., C. Duez, O. Fahy, A. Tsicopoulos, C. André, B. Wallaert, S. Lebecque, B. Tonnel, and J. Pestel. 2000. Human dendritic cells in the severe combined mmunodeficiency mouse model: their potentiating role in the allergic reaction. *Lab. Investig. J. Tech. Methods Pathol.* 80: 605-614.
14. Fahy, O., H. Porte, S. Sénéchal, H. Vorng, A. R. McEuen, M. G. Buckley, A. F. Walls, A. B. Tonnel, and A. Tsicopoulos. 2001. Chemokine-induced cutaneous inflammatory cell infiltration in a model of Hu-PBMC-SCID mice grafted with human skin. *Am. J. Pathol.* 158: 1053-1063.
15. Watanabe, R., A. Gehad, C. Yang, L. Campbell, J. E. Teague, C. Schlapbach, C. Elco, V. Huang, T. R. Matos, T. S. Kupper, and R. A. Clark. 2015. Human skin is protected by four functionally and phenotypically discrete populations of resident and recirculating memory T cells. *Sci. Transl. Med.* 7: 279ra39.
16. Acosta-Rodriguez, E. V., L. Rivino, J. Geginat, D. Jarrossay, M. Gattorno, A. Lanzavecchia, F. Sallusto, and G. Napolitani. 2007. Surface phenotype and antigenic specificity of human interleukin 17-producing T helper memory cells. *Nat. Immunol.* 8: 639-646.
17. Sanchez Rodriguez, R., M. L. Pauli, I. M. Neuhaus, S. S. Yu, S. T. Arron, H. W. Harris, S. H.-Y. Yang, B. A. Anthony, F. M. Sverdrup, E. Krow-Lucal, T. C. Mackenzie, D. S. Johnson, E. H. Meyer, A. Lohr, A. Hsu, J. Koo, W. Liao, R. Gupta, M. G. Debbaneh, D. Butler, M. Huynh, E. C. Levin, A. Leon, W. Y. Hoffman, M. H. McGrath, M. D. Alvarado, C. H. Ludwig, H.-A. Truong, M. M. Maurano, I. K. Gratz, A. K. Abbas, and M. D. Rosenblum. 2014. Memory regulatory T cells reside in human skin. *J. Clin. Invest.* 124: 1027-1036.
18. Lee, J., M. A. Brehm, D. Greiner, L. D. Shultz, and H. Kornfeld. 2013. Engrafted human cells generate adaptive immune responses to *Mycobacterium bovis* BCG infection in humanized mice. *BMC Immunol.* 14: 53.
19. Harui, A., S. M. Kiertscher, and M. D. Roth. 2011. Reconstitution of huPBL-NSG mice with donor-matched dendritic cells enables antigen-specific T-cell activation. *J. Neuroimmune Pharmacol. Off. J. Soc. Neuroimmune Pharmacol.* 6: 148-157.

The invention claimed is:

1. A rodent model for human diseases or disorders of the immune system, comprising an immunodeficient neutrophil depleted rodent host engrafted with a human skin equivalent (huSE) and human immune cells, wherein the rodent host is engrafted with huSE which comprises a cell slurry of human keratinocytes and fibroblasts free of skin-resident immune cells, and wherein the engrafted human immune cells infiltrate the huSE.

2. The model of claim 1, wherein the human immune cells are selected from the group consisting of T cells, B cells, natural killer cells, monocytes, monocyte derived dendritic cells, dendritic cells and their subtypes, tissue-derived dendritic cells, Langerhans cells, γδ-T cells, mast cells innate lymphoid cells (ILC), and human peripheral blood mononuclear cells (huPBMC).

3. The model of claim 1, wherein the host is a mouse.

4. The model of claim 3, wherein the host is an immunodeficient mouse.

5. The model of claim 4, wherein the host is selected from the group consisting of a NOD Scid common-γ chain$^{-/-}$ (NSG) mouse, a NOD Shi-scid common-γ chain$^{-/-}$ (NOG) mouse, and a BALB/cA-Rag2$^{-/-}$ IL2rgamma$^{-/-}$ (BRG) mouse.

6. The model of claim 1, wherein the human skin equivalent comprises human primary or immortalized keratinocytes and human primary or immortalized fibroblasts.

7. The model of claim 1, wherein the huSE and the immune cells are isolated from the same donor.

8. The model of claim 1, wherein the huSE and the immune cells are isolated from different donors.

9. The model of claim 1, wherein the host is a rat or hamster.

10. The model of claim 5, wherein the host is a NOD Scid common-γ chain$^{-/-}$ (NSG) mouse.

\* \* \* \* \*